United States Patent
Butters et al.

(10) Patent No.: US 8,915,925 B2
(45) Date of Patent: *Dec. 23, 2014

(54) PERCUTANEOUS COMPRESSION AND DISTRACTION SYSTEM

(71) Applicant: Stryker Spine, Cestas (FR)

(72) Inventors: Joshua A. Butters, Chandler, AZ (US); Jeffery Arnett, Gilbert, AZ (US)

(73) Assignee: Stryker Spine (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/942,071

(22) Filed: Jul. 15, 2013

(65) Prior Publication Data

US 2014/0018860 A1    Jan. 16, 2014

Related U.S. Application Data

(63) Continuation of application No. 13/419,919, filed on Mar. 14, 2012, now Pat. No. 8,506,574, which is a continuation of application No. 11/904,030, filed on Sep. 25, 2007, now Pat. No. 8,157,809.

(60) Provisional application No. 60/847,174, filed on Sep. 25, 2006.

(51) Int. Cl.
*A61B 17/58* (2006.01)
*A61B 17/60* (2006.01)
*A61F 2/00* (2006.01)
*A61B 17/70* (2006.01)
*A61B 17/02* (2006.01)

(52) U.S. Cl.
CPC ......... *A61B 17/7077* (2013.01); *A61B 17/7079* (2013.01); *A61B 17/7001* (2013.01); *A61B 2017/0256* (2013.01); *A61B 17/025* (2013.01)
USPC ......................................... 606/105; 606/104

(58) Field of Classification Search
USPC ............ 606/57, 104, 105; 600/213, 214, 227, 600/225; 81/391
See application file for complete search history.

(56) References Cited

U.S. PATENT DOCUMENTS 3,997,138 A   12/1976   Crock et al.
4,382,438 A    5/1983   Jacobs
(Continued)

FOREIGN PATENT DOCUMENTS

DE   29710979 U1   8/1997
DE   19726754 A1   2/1999
(Continued)

OTHER PUBLICATIONS

Charles Hartjen; The Atavi System, Surgical Technique Brochure. Endius, p. 1-I7, undated.

(Continued)

*Primary Examiner* — Andrew Yang
(74) *Attorney, Agent, or Firm* — Lerner, David, Littenberg, Krumholz & Mentlik, LLP

(57) ABSTRACT

A compression and distraction shaft assembly applies compression and distraction to bones including vertebrae. Shaft A assembly and shaft B assembly are attached together via a polyaxial fulcrum. The polyaxial fulcrum allows all rotational degrees of freedom between shaft A assembly and shaft B assembly. Such fulcrum, during compression and distraction, does not impart ancillary stresses or motion to vertebrae. An hourglass-shaped bore for engaging pliers is formed in approximately middle of both the shaft A assembly and the shaft B assembly. Distraction pliers having cylindrical tips are used to apply distraction to vertebrae. Once handles are pressed to impart an appropriate amount of distraction to the vertebrae, they are locked in this position. Compression pliers having cylindrical tips are used to apply compression to vertebrae. Once handles are pressed to impart an appropriate amount of compression to the vertebrae, they are locked in this position.

22 Claims, 11 Drawing Sheets

(56) References Cited

U.S. PATENT DOCUMENTS

| | | |
|---|---|---|
| 4,409,968 A | 10/1983 | Drummond |
| 4,411,259 A | 10/1983 | Drummond |
| 4,957,495 A | 9/1990 | Kluger |
| 5,010,879 A | 4/1991 | Moriya et al. |
| 5,059,194 A | 10/1991 | Michelson |
| 5,167,662 A | 12/1992 | Hayes et al. |
| 5,242,443 A | 9/1993 | Kambin |
| 5,281,223 A | 1/1994 | Ray |
| 5,385,565 A | 1/1995 | Ray |
| 5,478,340 A | 12/1995 | Kluger et al. |
| 5,487,743 A | 1/1996 | Laurain et al. |
| 5,591,167 A | 1/1997 | Laurain et al. |
| RE36,221 E | 6/1999 | Breard et al. |
| 6,090,113 A | 7/2000 | Le Couedic et al. |
| 6,123,707 A | 9/2000 | Wagner |
| 6,146,386 A | 11/2000 | Blackman et al. |
| 6,485,518 B1 | 11/2002 | Cornwall et al. |
| 6,506,151 B2 | 1/2003 | Estes et al. |
| 6,530,929 B1 | 3/2003 | Justis et al. |
| 6,616,666 B1 | 9/2003 | Michelson |
| 6,616,667 B1 | 9/2003 | Steiger et al. |
| 6,712,818 B1 | 3/2004 | Michelson |
| 7,008,422 B2 | 3/2006 | Foley et al. |
| 7,011,660 B2 | 3/2006 | Sherman et al. |
| 7,188,626 B2 | 3/2007 | Foley et al. |
| 2003/0055430 A1 | 3/2003 | Kim |
| 2003/0073998 A1 | 4/2003 | Pagliuca et al. |
| 2003/0187436 A1 | 10/2003 | Bolger et al. |
| 2004/0034351 A1 | 2/2004 | Sherman et al. |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0172022 A1 | 9/2004 | Landry et al. |
| 2004/0215190 A1 | 10/2004 | Nguyen et al. |
| 2004/0260287 A1 | 12/2004 | Ferree |
| 2005/0010220 A1 | 1/2005 | Casutt et al. |
| 2005/0010221 A1 | 1/2005 | Dalton |
| 2005/0021030 A1 | 1/2005 | Pagliuca et al. |
| 2005/0021031 A1 | 1/2005 | Foley et al. |
| 2005/0038436 A1 | 2/2005 | Michelson |
| 2005/0070917 A1 | 3/2005 | Justis |
| 2005/0090822 A1 | 4/2005 | DiPoto |
| 2005/0090833 A1 | 4/2005 | DiPoto |
| 2005/0131421 A1 | 6/2005 | Anderson et al. |
| 2005/0131422 A1 | 6/2005 | Anderson et al. |
| 2005/0154389 A1 | 7/2005 | Selover et al. |
| 2005/0245928 A1 | 11/2005 | Colleran et al. |
| 2006/0111714 A1 | 5/2006 | Foley |
| 2006/0200135 A1 | 9/2006 | Sherman et al. |
| 2006/0264934 A1 | 11/2006 | Fallin |

FOREIGN PATENT DOCUMENTS

| | | |
|---|---|---|
| DE | 10027988 | 1/2002 |
| EP | 0528177 | 2/1993 |
| EP | 611116 | 8/1994 |
| EP | 665731 | 8/1995 |
| SU | 839513 | 6/1981 |
| WO | 94/09726 | 5/1994 |
| WO | 0141681 A1 | 6/2001 |
| WO | 2004021899 | 3/2004 |
| WO | 2004037074 | 5/2004 |
| WO | 2004041100 | 5/2004 |
| WO | 2004080318 A1 | 9/2004 |
| WO | 2005018466 | 3/2005 |
| WO | 2005023123 | 3/2005 |
| WO | 2005/032358 | 4/2005 |
| WO | 2005060534 | 7/2005 |
| WO | 2005060534 A | 7/2005 |
| WO | 2006060430 | 6/2006 |

OTHER PUBLICATIONS

Diapason, Surgical Technique Catalog, Diapasan Spinal System, Jan. 2002.

Kambin et al, "Percutaneous Posterolateral Lumbar Discectomy and Decompression with a 6.9-millimeter cannula", The Journal of Bone and Joint Surgery, pp. 822-831, Jul. 1991.

Kambin, Minimally Invasive Techniques in Spinal Surgery Current Practice, Neurosurgical Focus, wwwspineuniversecom, 16 pages, printed Aug. 24, 2005.

Leu et al., Percutaneous Fusion of the Lumbar Spine, State of the Art Reviews, vol. 6, No. 3, pp. 593-604, Sep. 1992.

Pathfinder; Minimally Invasive Pedicle Fixation System. Spinal Concepts Product Brochure p. 1-4, May 2003.

U.S. Appl. No. 11/178,035, filed Jul. 8, 2005.

U.S. Appl. No. 11/526,785, filed Sep. 25, 2006.

U.S. Appl. No. 12/316,637, filed Dec. 15, 2008.

U.S. Appl. No. 11/904,029, filed Sep. 25, 2007.

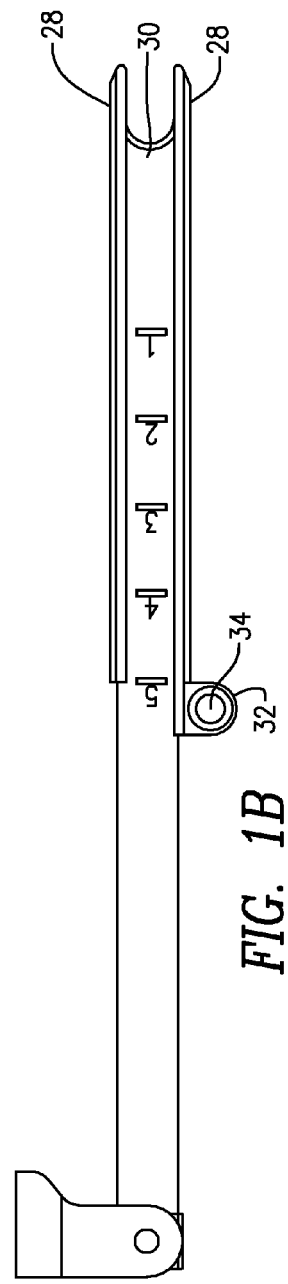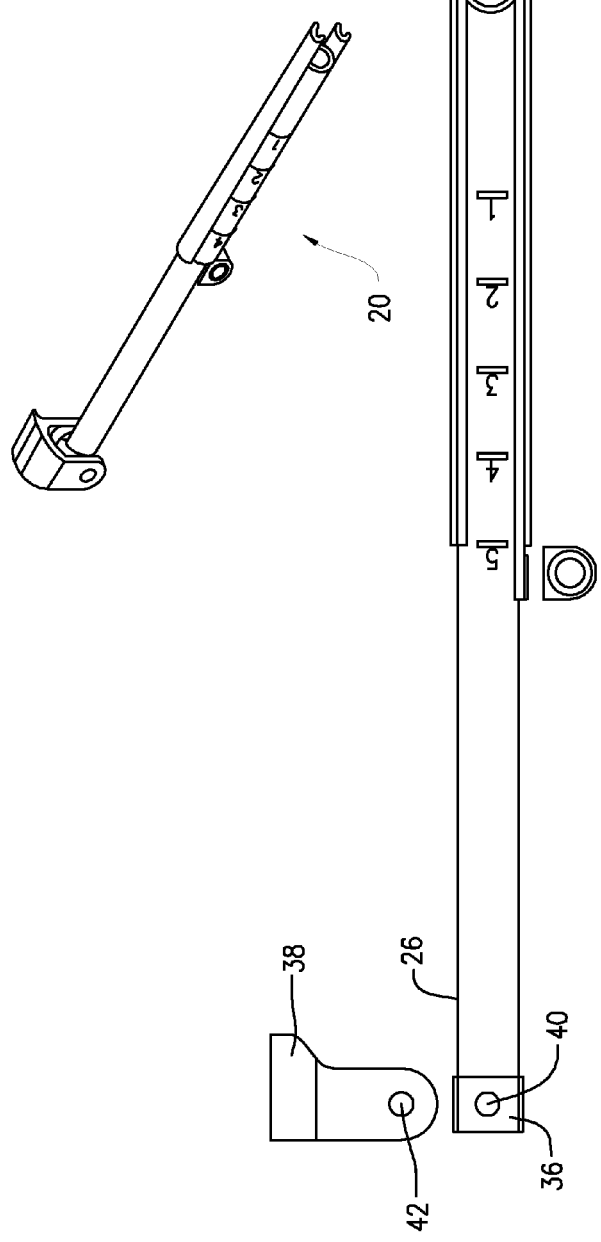

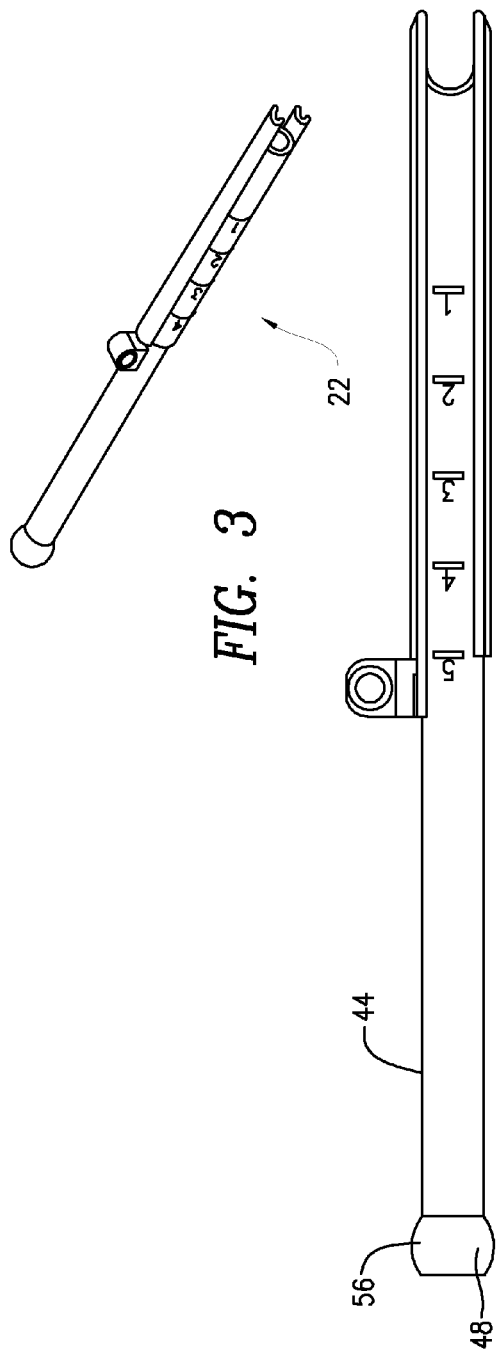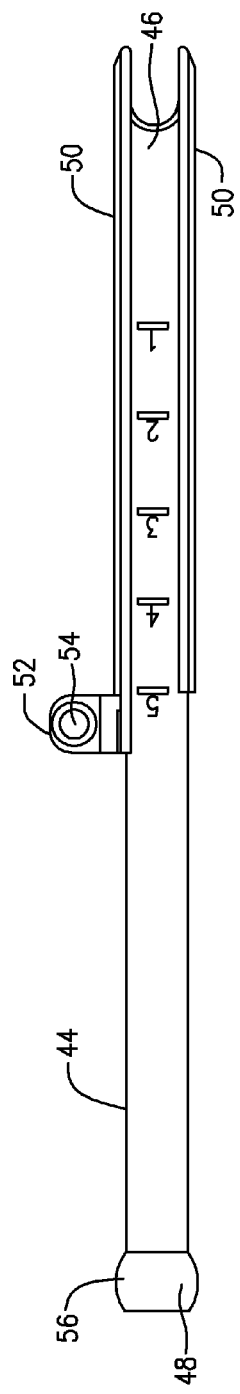
FIG. 3
FIG. 3A
FIG. 3B

PERCUTANEOUS COMPRESSION AND DISTRACTION SYSTEM

CROSS-REFERENCE TO RELATED APPLICATIONS

The present application is a continuation of U.S. patent application Ser. No. 13/419,919, filed Mar. 14, 2012, which is a continuation of U.S. patent application Ser. No. 11/904,030, filed Sep. 25, 2007, which claims the benefit of the filing date of U.S. Provisional Patent Application No. 60/847,174, filed Sep. 25, 2006, the disclosures of which are hereby incorporated herein by reference.

BACKGROUND OF THE INVENTION

The present invention relates to a percutaneous compression and distraction system, more particularly to a system for percutaneous compression or distraction of vertebral bodies via pedicle screws.

BRIEF DESCRIPTION OF THE PRIOR ART

Various compression pliers and distraction devices are available to impart compression or distraction forces to bones. However, these devices fail to allow for all rotational degrees of freedom so as to not over constrain the desired compression or distraction motion and therefore fail to function appropriately when the trajectories of the compression and distraction shafts are non-coplanar. Therefore, there is a need for a compression and distraction system that provides a polyaxial fulcrum point that does not over constrain the motion and at the same time provides high mechanical advantage during compression and distraction of vertebral elements.

SUMMARY OF THE INVENTION

The present invention provides a compression and distraction shaft A assembly and a compression and distraction shaft B assembly. An assembly of the shaft A assembly and shaft B assembly forms a compression and distraction shaft assembly used to apply compression and distraction to bones including vertebrae. Shaft A assembly and shaft B assembly are attached together in use via a polyaxial fulcrum. The polyaxial fulcrum allows all rotational degrees of freedom between shaft A assembly and shaft B assembly. Such fulcrum, during compression and distraction, does not impart ancillary stresses or motion to vertebrae. An hourglass-shaped bore for engaging pliers is formed in approximately middle of both the shaft A assembly and the shaft B assembly.

Distraction pliers having cylindrical tips are used to apply distraction to vertebrae. The tips of the distraction pliers are inserted in hourglass-shaped bores and handles of the pliers pressed together to move the tips away from each other. This results in distraction of the vertebrae that are connected to the arcuate-shaped end of the shaft A assembly and shaft B assembly. Once handles are pressed to impart an appropriate amount of distraction to the vertebrae, they are locked in this position.

Compression pliers having cylindrical tips are used to apply compression to vertebrae. The tips of the compression pliers are inserted in hourglass-shaped bores and handles of the pliers pressed together to move the tips towards each other. This results in compression of the vertebrae that are connected to the arcuate-shaped end of the shaft A assembly and shaft B assembly. Once handles are pressed to impart an appropriate amount of compression to the vertebrae, they are locked in this position.

An object of the preset invention is to provide a bone compression system having a first shaft and a second shaft. The first shaft has a first end and the second shaft has a second end. The first shaft is adapted to engage with an attachment to a first bone and the second shaft adapted to engage with an attachment to a second bone. The system includes compression pliers for compressing together the first shaft and the second shaft. The compression pliers engage the first shaft and the second shaft such that the first shaft and the second shaft can move in all directions independent of each other.

Another object of the invention is to provide a bone distraction system having a first shaft and a second shaft. The first shaft has a first end and the second shaft has a second end. The first end of the first shaft and the second end of the second shaft are adapted to mate with each other to provide a polyaxial fulcrum point about which the first shaft and the second shaft articulate. The system also includes distraction pliers for distracting the first shaft and the second shaft from each other. The distraction pliers engage the first shaft and the second shaft such that the movement of the polyaxial fulcrum is not restricted by the distraction pliers.

Another object of the invention is to provide a bone compression and distraction system that includes all the components of the bone compression and bone distraction system described above.

Another object of the invention is to provide a method of compressing or distracting vertebral bodies. The method includes providing a first pedicle screw, a second pedicle screw, a compression and a distraction device. The compression and the distraction device each have a first shaft having a first end and a second end and a second shaft having a third end and a fourth end. The first end of the first shaft and the third end of the second shaft are mated with each other to provide a polyaxial fulcrum point about which the first shaft and the second shaft articulate. The second end of the first shaft and the fourth end of the second shaft are engaged with the first pedicle screw and the second pedicle screw respectively. Compression pliers or distraction pliers are engaged with the first shaft and the second shaft, and the vertebrae are compressed or distracted by operating the pliers.

BRIEF DESCRIPTION OF THE DRAWINGS

FIG. 1 is an isometric view of compression and distraction shaft A subassembly.

FIGS. 1A and 1B are side views of the shaft A subassembly.

FIG. 3 is an isometric view of compression and distraction shaft B subassembly.

FIGS. 3A and 3B are side views of the shaft B subassembly.

DETAILED DESCRIPTION OF THE PREFERRED EMBODIMENTS

FIGS. 1, 1A and 1B show a compression and distraction shaft A assembly 20. FIGS. 3, 3A and 3B show a compression and distraction shaft B assembly 22. A further assembly of the shaft A assembly 20 and shaft B assembly 22 forms a compression and distraction shaft assembly 24 seen in FIGS. 5, 5A, 6 and 6A.

Figure 2:
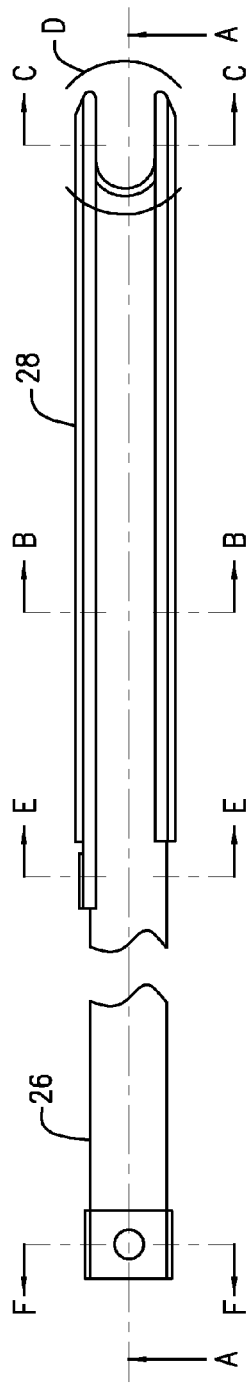
FIG. 2 is a side view of the shaft of FIG. 1.
Figure 2A:
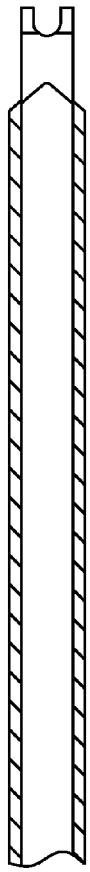
FIG. 2A is a top view of the shaft of FIG. 1.
Figure 2B:
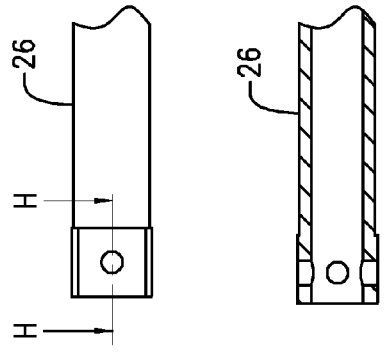
FIG. 2B is a sectional view along line A-A of shaft of FIG. 1.

Assembly 20 includes a shaft 26. FIG. 2 shows the details of construction of shaft 26. Shaft 26 has two long plates 28 attached to it in diametrically opposed location. One end of each of the plates 28 overhangs from the first end 30 of shaft 26. The overhanging portions are located opposite each other and have an arcuate shape at the very tip. The arcuate shape allows shaft 26 to lay over a rod that may be implanted on the vertebrae.

A tab 32 is attached in approximately middle of shaft 26. Tab 32 has a bore 34. Bore 34 has an hourglass shape along its central axis. A second end 36 of shaft 26 is on the opposing side from end 30. A fulcrum 38 is attached at second end 36. The means for attaching fulcrum 38 may be a bore 40 formed in shaft 26 and bore 42 formed in fulcrum 38 with a pin driven through bores 40 and 42 to connect fulcrum 38 to shaft 26.

Figure 4:
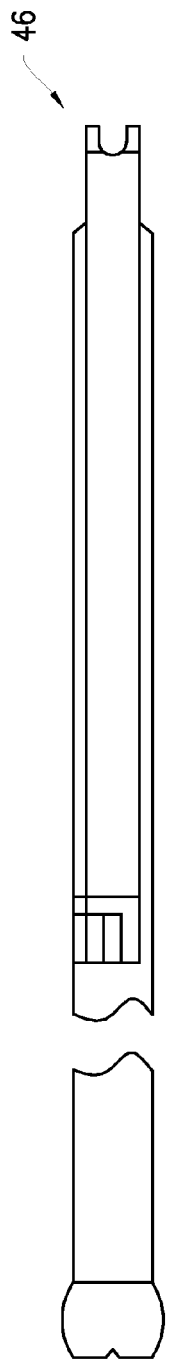
FIG. 4 is a side view of the shaft of FIG. 3.
Figure 4A:
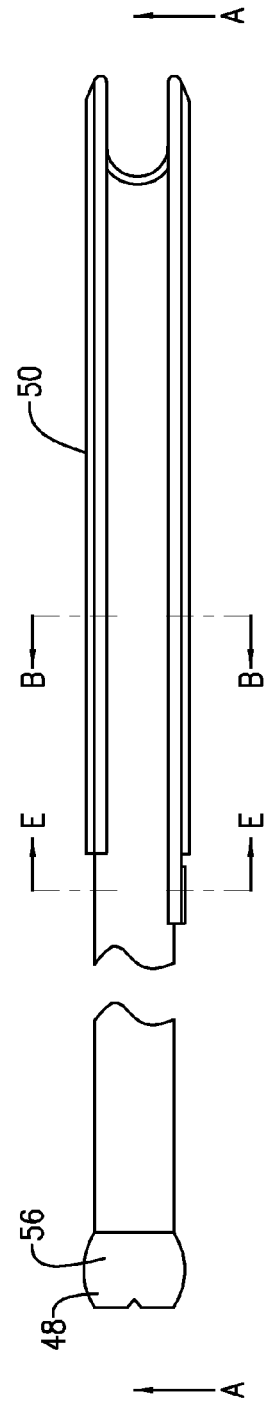
FIG. 4A is a top view of the shaft of FIG. 3.
Figure 4B:
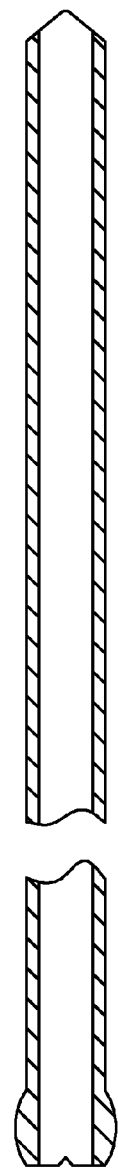
FIG. 4B is a sectional view along line A-A of shaft of FIG. 3.
Figure 5:
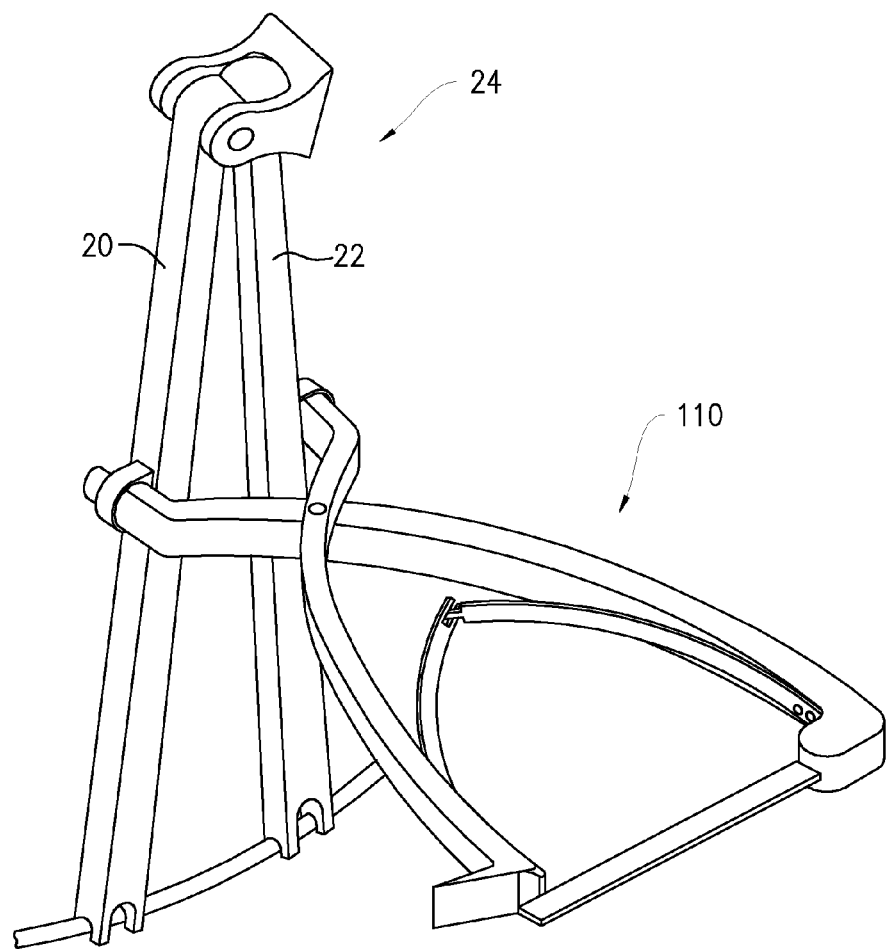
FIG. 5 shows compression pliers engaged with compression distraction shafts.
Figure 5A:
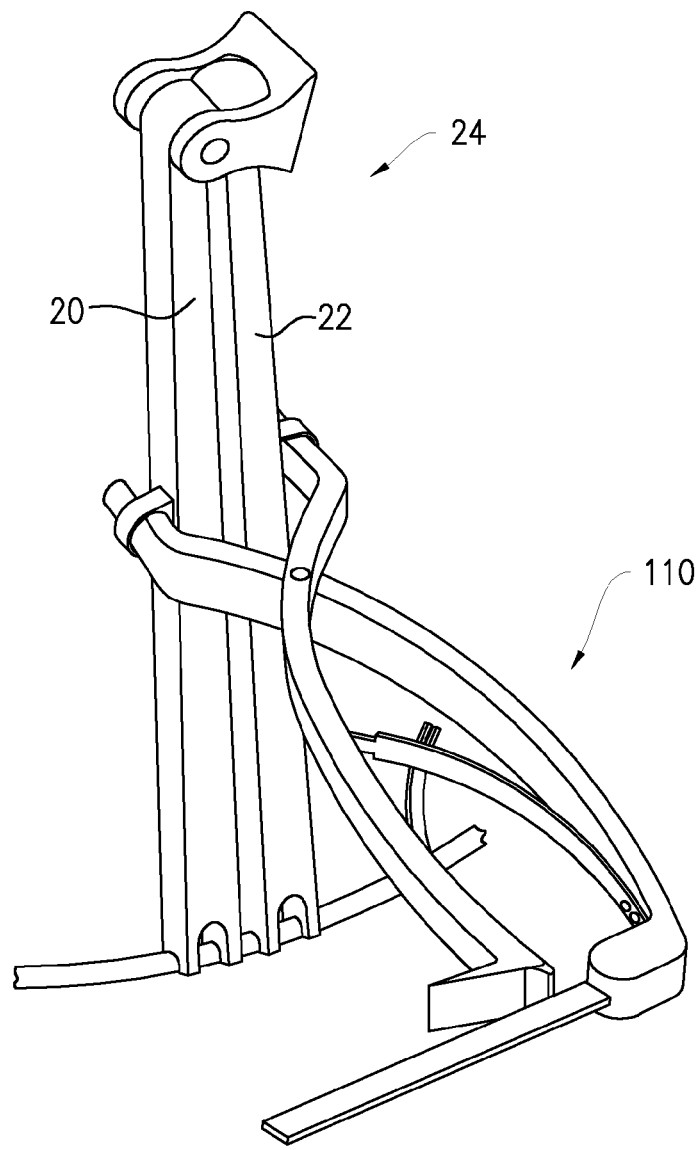
FIG. 5A also shows compression pliers engaged with compression distraction shafts.
Figure 6:
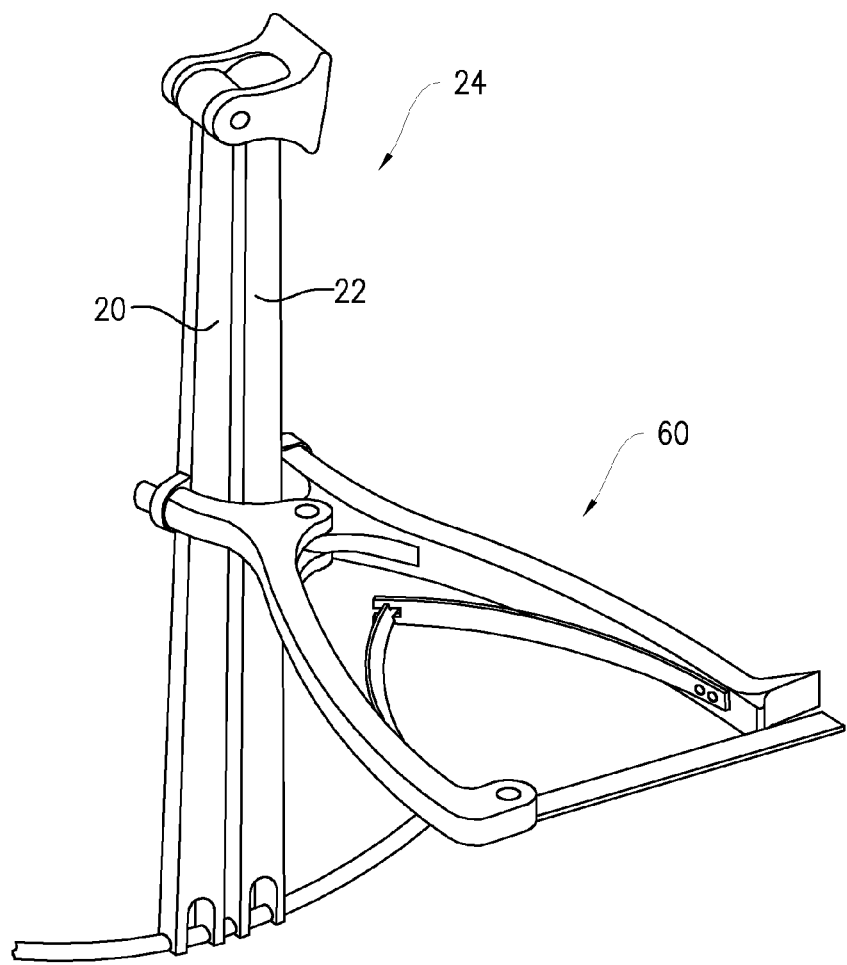
FIG. 6 shows distraction pliers engaged with compression distraction shafts.
Figure 6A:
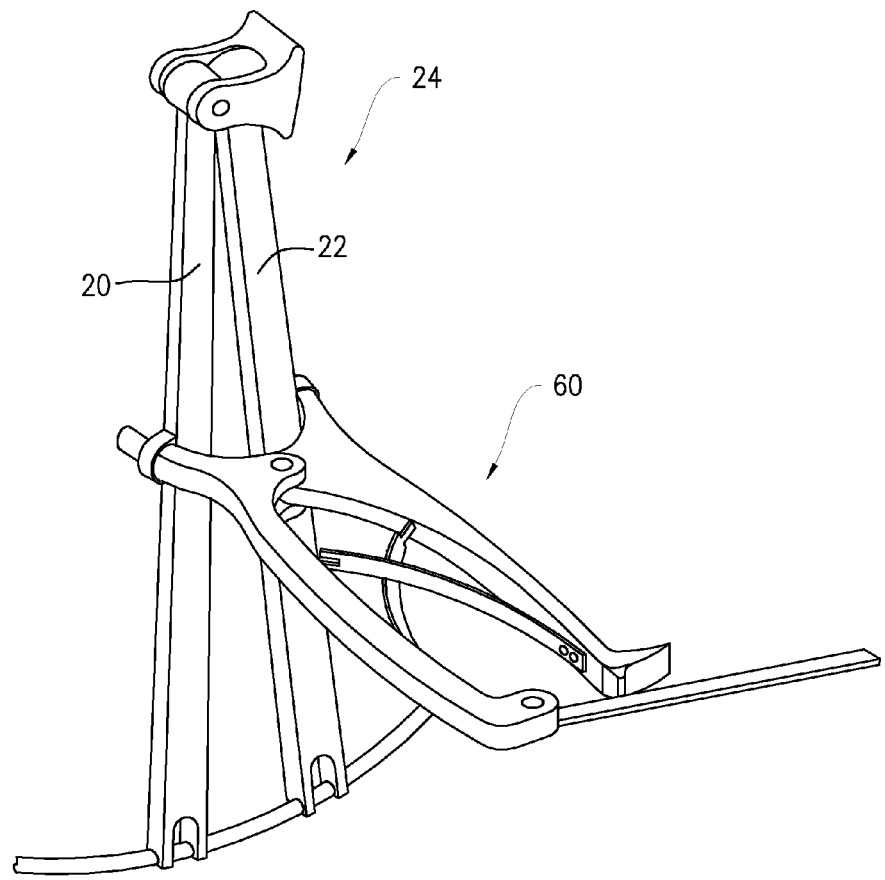
FIG. 6A also shows distraction pliers engaged with compression distraction shafts.

Assembly 22 includes a shaft 44. FIGS. 4, 4A and 4B show the details of construction of shaft 44. Shaft 44 has a first end 46 and a second end 48. First end 46 is similar in construction to first end 30 of shaft 26. Shaft 44 has two long plates 50 attached to it in diametrically opposed location. One end of each of the plates 50 overhangs from the first end 46 of shaft 44. The overhanging portions are located opposite each other and have an arcuate shape at the very tip. The arcuate shape allows shaft 44 to lay over a rod that may be implanted on a vertebrae.

A tab 52 is attached in approximately middle of shaft 44. Tab 52 has a bore 54. Bore 54 has an hourglass shape along its central axis. A ball 56 is formed at second end 48. Ball 56 mates with fulcrum 38 to form a polyaxial fulcrum point. When shaft 26 and shaft 44 are assembled by inserting ball 56 in fulcrum 38 a poly axial fulcrum that allows all rotational degrees of freedom is formed. Such fulcrum, during compression and distraction, does not impart ancillary stresses or motion to vertebrae.

Figure 7:
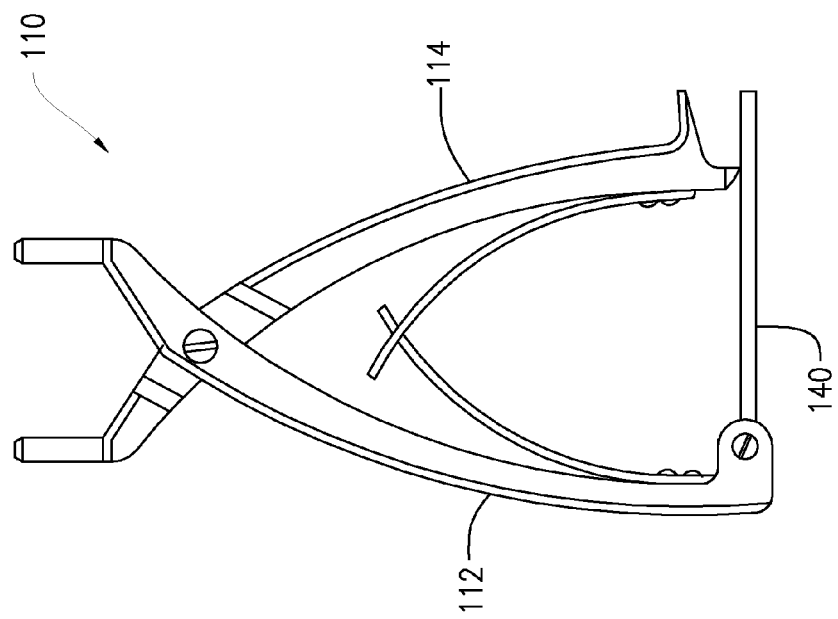
FIG. 7 is an assembly drawing showing a distraction pliers assembly.
Figure 7A:
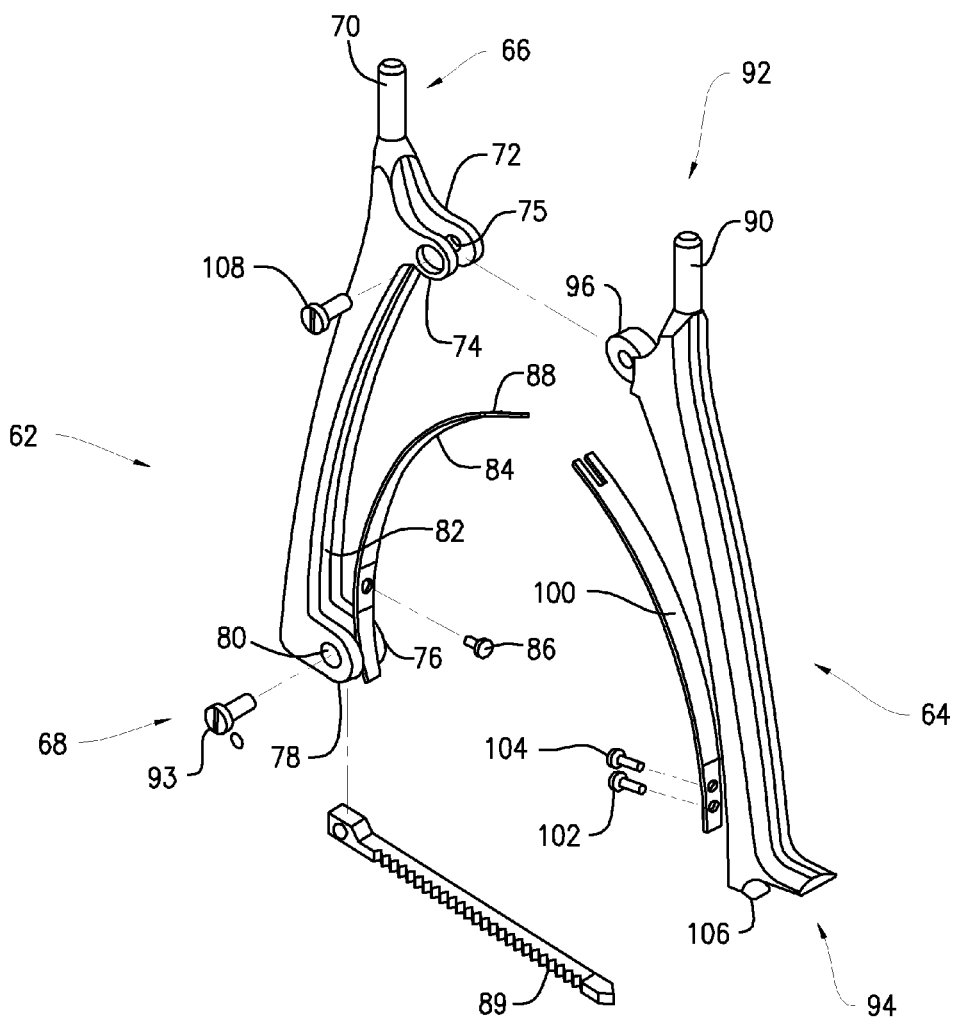
FIG. 7A shows details of the distraction pliers assembly of FIG. 7.

FIGS. 7 and 7A show distraction pliers 60. Distraction pliers 60 have a first handle 62 and a second handle 64. First handle 62 has a tip end 66 and a ratchet end 68. First handle 62 has an elongate shape with a cylindrical tip 70 formed at tip end 66. At a distance below tip end 66 two tabs 72 and 74 extend from the body of first handle 62. Tabs 72 and 74 are parallel to each other and have a bore 75 formed through them. The handle end opposing tip end 66 also has two tabs 76 and 78 extend from the body of first handle 62. A bore 80 is formed through tabs 76 and 78. A screw hole 82 is formed at a distance from the ratchet end and above tabs 76 and 78. A leaf spring 84 is attached to first handle 62 by inserting a screw 86 in a hole in leaf spring 84 and threading screw 86 in screw hole 82. Leaf spring 82 has a far end that projects away from first handle 62. The far end has a notch 88 formed at its tip. A ratchet 89 is attached to ratchet end 68 of the first handle 62. The ratchet 89 has a bore 91 that aligns with bore 80 in tabs 76 and 78. A pin 93 is driven through bores 80 and 91 to attach ratchet 89 to first handle 62. Ratchet 89 has triangular projections formed on its surface.

Second handle 64 has a tip end 92 and a ratchet end 94. Second handle 64 has an elongate shape with a cylindrical tip 90 formed at tip end 92. At a distance below tip end 92 a tab 96 extends from the body of second handle 64. Tab 96 has a bore 98 formed through it. A leaf spring 100 is attached to second handle 64. Second handle 64 has two screw holes (not shown) formed above the ratchet end 94. Leaf spring 100 is attached to second handle 64 by threading two screws 102 and 104 via two holes in leaf spring 100 and into the screw holes in second handle 64. Leaf spring 100 has a far end that projects away from first handle 64. Leaf spring 100 has notch 108 formed at its tip. Notch 108 engages notch 88 thereby engaging leaf springs 84 and 100. When engaged, leaf springs 84 and 100 keep the distraction pliers biased in a closed position. A tooth 106 is formed at the tip of ratchet end 94. First handle 62 and second handle 64 are rotatably joined together by aligning bores 75 and 80 and inserting a screw 108 through them.

In use, cylindrical tips 70 and 90 are inserted in hourglass-shaped bores 34 and 54 and first handle 62 and second handle 64 pressed together. When the first handle 62 and the second handle 64 are pressed together, the cylindrical tip 70 and 90 are moved away from each other. This results in distraction of the vertebrae that are connected to the arcuate-shaped end of the shaft A assembly 20 and shaft B assembly 22. The connection between the arcuate end of the shaft assemblies 20 and 22 and the vertebrae may be made in any known manner. For example, each of the shaft assemblies 20 and 22 may be connected to a cup of a pedicle screw mounted on the vertebra via a latch or a threaded connection. Once first handle 62 and second handle 64 are pressed to impart an appropriate amount of distraction to the vertebrae, they are locked in this position. Tooth 106 engages ratchet 89 to lock first handle 62 and second handle 64 in their pressed position, thereby holding the vertebrae in a distracted position while the surgeon fixes a rod in the pedicle screws.

Figure 8:
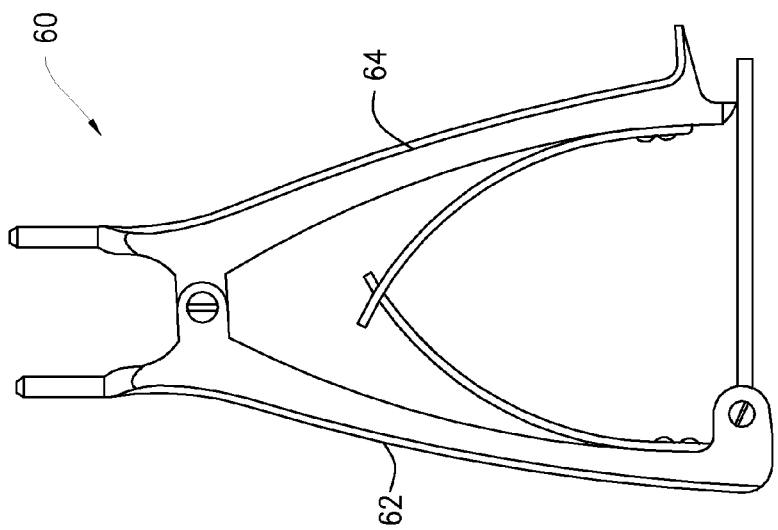
FIG. 8 is an assembly drawing of a compression pliers assembly.
Figure 8A:
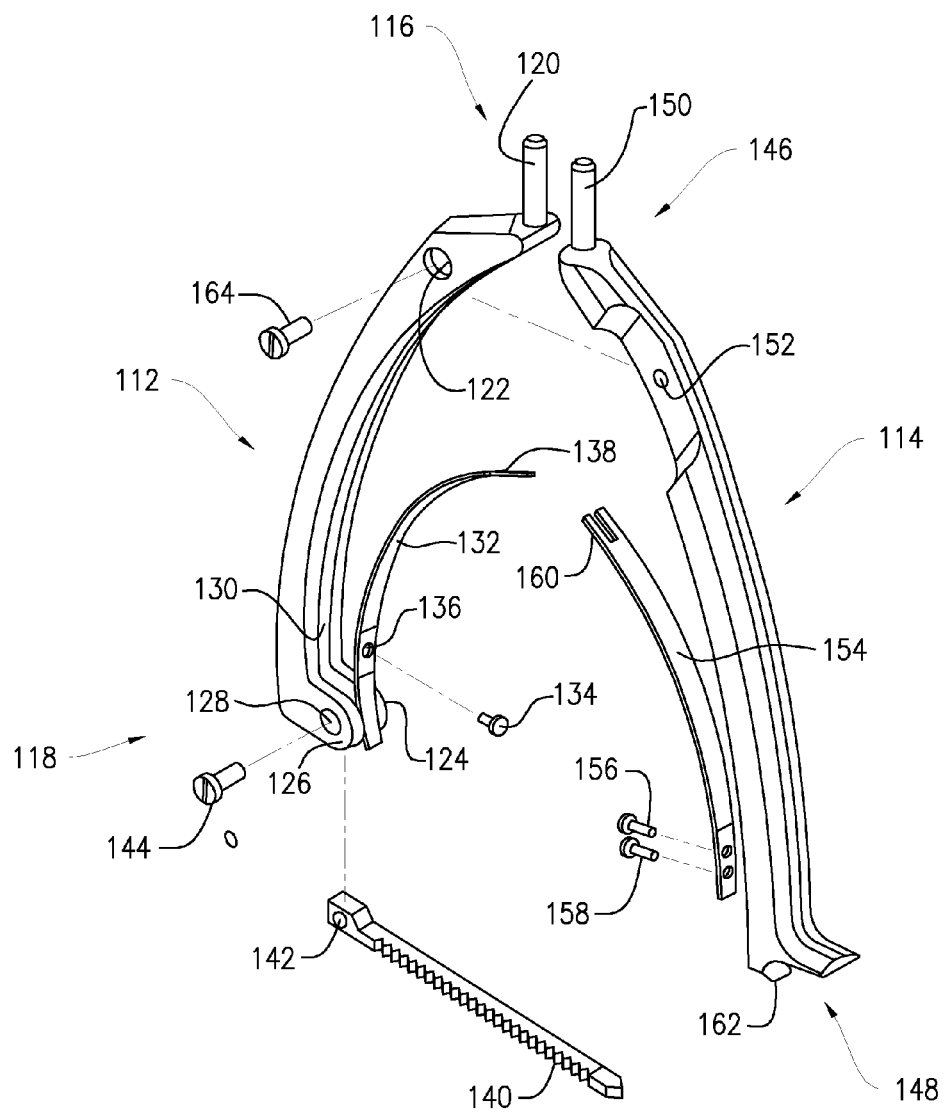
FIG. 8A shows details of the compression pliers assembly of FIG. 8.

FIGS. 8 and 8A show compression pliers 110. Compression pliers 110 have a third handle 112 and a fourth handle 114. Third handle 112 has a tip end 116 and a ratchet end 118. A cylindrical tip 120 is formed at tip end 116. A hole 122 is formed in the body of third handle 112 below tip end 116. The end of third handle 112 opposing tip end 116 has two tabs 124 and 126. A bore 128 is formed through tabs 124 and 126. A screw hole 130 is formed in body of third handle 112 above tabs 124 and 126. A leaf spring 132 is attached to third handle 112 by inserting a screw 134 in a hole 136 formed in leaf spring 132 and threading the screw in the hole 130. Leaf spring 132 has a far end that projects away from third handle 112. The far end has a notch 138 formed at its tip. A ratchet 140 is attached to ratchet end 118 of the third handle 112. The ratchet 140 has a bore 142 that aligns with bore 128 in tabs 124 and 126. A pin 144 is driven through bores 128 and 142 to attach ratchet 140 to third handle 112. Ratchet 140 has triangular projections formed on its surface.

Fourth handle 114 has a tip end 146 and a ratchet end 148. Fourth handle 114 has a cylindrical tip 150 formed at tip end 146. At a distance below tip end 146 a bore 152 is formed in the body of third handle 114. A leaf spring 154 is attached to fourth handle 114. Fourth handle 114 has two screw holes (not shown) formed above the ratchet end 148. Leaf spring 154 is attached to fourth handle 114 by threading two screws 156 and 158 via two holes in leaf spring 154 and into the screw holes in fourth handle 114. Leaf spring 154 has a far end that projects away from fourth handle 114. Leaf spring 154 has notch 160 formed at its tip. Notch 160 engages notch 138 thereby engaging leaf springs 154 and 132. When engaged, leaf springs 132 and 154 keep the compression pliers biased in an open position. A tooth 162 is formed at the tip of ratchet end 148. Third handle 112 and fourth handle 114 are rotatably joined together by aligning bores 122 and 152 and inserting a screw 164 through them.

In use, cylindrical tips 120 and 150 are inserted in hourglass-shaped bores 34 and 54 and third handle 112 and fourth handle 114 pressed together. When the third handle 112 and fourth handle 114 are pressed together, cylindrical tips 120 and 150 are moved towards each other. This results in compression of the vertebrae that are connected to the arcuate-shaped end of the shaft assembly 20 and shaft assembly 22. The connection between the arcuate end of the shaft assemblies 20 and 22 and the vertebrae may be made in any known manner. For example, each of the shaft assemblies 20 and 22 may be connected to a cup of a pedicle screw mounted on the vertebrae via a latch or a threaded connection. Once third handle 112 and fourth handle 114 are pressed to impart an appropriate amount of compression to the vertebrae, they are locked in this position. Tooth 162 engages ratchet 140 to lock third handle 112 and fourth handle 114 in their pressed position, thereby holding the vertebrae in compressed position while the surgeon fixes a rod in the pedicle screws.

The compression and distraction pliers may also be used with compression distraction shafts that are not attached to each other. These shafts can be attached rigidly to the tips of the compression or distraction pliers and impart compression or distraction to the bones. The compression and distraction system may also be used with minimally invasive surgery as described, for example, in commonly assigned U.S. Patent Application Publication No. 2007/0233079, entitled "Rod Contouring Apparatus And Method For Percutaneous Pedicle Screw Extension," which is incorporated herein by reference in its entirety.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of displacing vertebral bodies, comprising:
   connecting a first end of a first shaft to a first pedicle screw mounted to a first vertebra of a spine, the first shaft having a second end opposite the first end;
   connecting a third end of a second shaft to a second pedicle screw mounted to a second vertebra of the spine, the second shaft having a fourth end opposite the third end;
   removably engaging a first member of a displacement device to a central portion of the first shaft intermediate the first and second ends of the first shaft;
   removably engaging a second member of the displacement device to a central portion of the second shaft intermediate the third and fourth ends of the second shaft; and
   actuating the displacement device to move the first and second members of the displacement device relative to one another, thereby imparting forces to the first and second shafts to displace the first and second vertebrae with respect to one another.

2. The method of claim 1, wherein the step of actuating the displacement device comprises moving the first and second members towards one another to compress together the first and second vertebrae.

3. The method of claim 1, wherein the step of actuating the displacement device comprises moving the first and second members away from one another to distract apart the first and second vertebrae.

4. The method of claim 1, wherein the step of removably engaging the first member of the displacement device to the first shaft comprises removably connecting the first member of the displacement device to a connector of the first shaft, and wherein the step of removably engaging the second member of the displacement device to the second shaft comprises removably connecting the second member of the displacement device to a connector of the second shaft.

5. The method of claim 4, wherein the step of removably connecting the first member of the displacement device to the connector of the first shaft comprises inserting a portion of the first member of the displacement device into an opening of the connector of the first shaft, and wherein the step of removably connecting the second member of the displacement device to the connector of the second shaft comprises inserting a portion of the second member of the displacement device into an opening of the connector of the second shaft.

6. The method of claim 1, further comprising providing a second displacement device, wherein actuating the first displacement device moves the first and second vertebrae away from one another, and actuating the second displacement device moves the first and second vertebrae towards one another.

7. The method of claim 1, further comprising connecting the second end of the first shaft to the fourth end of the second shaft.

8. The method of claim 7, wherein the step of connecting the second end of the first shaft to the fourth end of the second shaft comprises providing a fulcrum proximate the second end of the first shaft and the fourth end of the second shaft about which the first shaft and the second shaft are pivotable with respect to one another.

9. The method of claim 1, wherein the first member of the displacement device includes an end of a first arm, wherein the second member of the displacement device comprises an end of a second arm, the first and second arms being pivotably coupled together at a pivot point, and wherein the step of actuating the displacement device comprises pivoting the first and second arms relative to one another about the pivot point.

10. The method of claim 1, wherein, during the step of actuating the displacement device, the displacement device extends laterally from the first and second shafts.

11. A method of moving first and second vertebrae, comprising:
   engaging a first component of a displacement device with a first central portion of a first shaft connected to a first pedicle screw in the first vertebra;
   engaging a second component of the displacement device with a second central portion of a second shaft connected to a second pedicle screw in the second vertebra; and
   actuating the displacement device to move the first and second vertebrae.

12. The method of claim 11, further comprising the steps of:
   connecting a first end of the first shaft with the first pedicle screw, the first shaft including a second end opposite the first end and the first central portion located between the first and second ends; and connecting a third end of the second shaft with the second pedicle screw, the second shaft including a fourth end opposite the third end and the second central portion located between the third and fourth ends.

13. The method of claim 12, further comprising the steps of:
  inserting the first pedicle screw in the first vertebra; and
  inserting the second pedicle screw in the second vertebra.

14. The method of claim 11, wherein the first and second components of the displacement device are pivotally connected to one another.

15. The method of claim 14, wherein the actuating step includes moving the first and second vertebrae towards one another.

16. The method of claim 14, wherein the actuating step includes moving the first and second vertebrae away from one another.

17. The method of claim 14, wherein the connecting steps include inserting a portion of the first component in a first connector of the first shaft and inserting a portion of the second component in a second connector of the second shaft.

18. The method of claim 12, further comprising the step of connecting the second and fourth ends of the first and second shafts.

19. The method of claim 18, wherein the step of connecting the second and fourth ends of the first and second shafts comprises pivotably connecting the second and fourth ends.

20. The method of claim 11, wherein the displacement device extends laterally from the first and second shafts during the actuating step.

21. A method of displacing vertebral bodies, comprising:
  connecting a first end of a first shaft to a first pedicle screw mounted to a first vertebra of a spine, the first shaft having a second end opposite the first end;
  connecting a third end of a second shaft to a second pedicle screw mounted to a second vertebra of the spine, the second shaft having a fourth end opposite the third end;
  removably connecting a first member of a displacement device to a connector of the first shaft intermediate the first and second ends of the first shaft;
  removably connecting a second member of the displacement device to a connector of the second shaft intermediate the third and fourth ends of the second shaft; and
  actuating the displacement device to move the first and second members of the displacement device relative to one another, thereby imparting forces to the first and second shafts to displace the first and second vertebrae with respect to one another.

22. The method of claim 21, wherein the step of removably connecting the first member of the displacement device to the connector of the first shaft comprises inserting a portion of the first member of the displacement device into an opening of the connector of the first shaft, and wherein the step of removably connecting the second member of the displacement device to the connector of the second shaft comprises inserting a portion of the second member of the displacement device into an opening of the connector of the second shaft.

* * * * *